US011452505B2

(12) United States Patent
Adachi et al.

(10) Patent No.: US 11,452,505 B2
(45) Date of Patent: Sep. 27, 2022

(54) ULTRASONIC DIAGNOSTIC APPARATUS AND ULTRASONIC DIAGNOSTIC SYSTEM

(71) Applicant: SOCIONEXT INC., Kanagawa (JP)

(72) Inventors: Naoto Adachi, Yokohama (JP); Naoto Yoneda, Yokohama (JP); Masaya Tamamura, Yokohama (JP); Amane Inoue, Yokohama (JP)

(73) Assignee: SOCIONEXT INC., Kanagawa (JP)

( * ) Notice: Subject to any disclaimer, the term of this patent is extended or adjusted under 35 U.S.C. 154(b) by 0 days.

(21) Appl. No.: 16/923,229

(22) Filed: Jul. 8, 2020

(65) Prior Publication Data
US 2020/0337682 A1 Oct. 29, 2020

Related U.S. Application Data

(63) Continuation of application No. PCT/JP2018/000515, filed on Jan. 11, 2018.

(51) Int. Cl.
*A61B 8/08* (2006.01)
*A61B 8/00* (2006.01)

(52) U.S. Cl.
CPC .......... *A61B 8/5207* (2013.01); *A61B 8/4444* (2013.01); *A61B 8/4461* (2013.01)

(58) Field of Classification Search
CPC ... A61B 8/5207; A61B 8/4444; A61B 8/4461; A61B 8/54; G01S 7/52085; G01S 7/5202; G01S 7/52096; G01S 15/8927
See application file for complete search history.

(56) References Cited

U.S. PATENT DOCUMENTS

| 2012/0203105 A1 | 8/2012 | Yamamoto et al. |
| 2015/0257701 A1 | 9/2015 | Horinaka et al. |
| 2015/0320396 A1* | 11/2015 | Abe ............ G01S 7/52077 600/443 |

(Continued)

FOREIGN PATENT DOCUMENTS

| JP | 2005-110934 A | 4/2005 |
| JP | 2012-019804 A | 2/2012 |

(Continued)

OTHER PUBLICATIONS

International Search Report of International Patent Application No. PCT/JP2018/000515 dated Apr. 10, 2018, with English translation of relevlant part.

(Continued)

*Primary Examiner* — Joseph M Santos Rodriguez
*Assistant Examiner* — Kaitlyn E Sebastian
(74) *Attorney, Agent, or Firm* — McDermott Will & Emery LLP

(57) ABSTRACT

An ultrasonic diagnostic apparatus includes a probe configured to transmit ultrasonic waves to a living body and receive ultrasonic waves reflected by the living body; and a processor configured to, in a moving image mode, cause ultrasonic image data based on ultrasonic waves received by a first subset of the total number of oscillators that the probe has to be output, and, in a static image mode, cause ultrasonic image data based on ultrasonic waves received by a second subset of the total number of oscillators that the probe has to be output, wherein the number of oscillators used in the second subset is greater than the number of oscillators used in the first subset.

11 Claims, 11 Drawing Sheets

(56) References Cited

U.S. PATENT DOCUMENTS

2017/0071579 A1\* 3/2017 Ko .................... A61B 8/4488
2017/0164835 A1\* 6/2017 Wiest ................. G01S 15/8997
2017/0258448 A1\* 9/2017 Maruyama .......... G01S 7/52079

FOREIGN PATENT DOCUMENTS

JP          2012-161555 A      8/2012
JP          2015-173828 A      10/2015

OTHER PUBLICATIONS

Written Opinion of The International Searching Authority of International Application No. PCT/JP2018/000515 dated Apr. 10, 2018, with translation of the relevant part.

\* cited by examiner

ULTRASONIC DIAGNOSTIC APPARATUS AND ULTRASONIC DIAGNOSTIC SYSTEM

CROSS-REFERENCE TO RELATED APPLICATION

The present application is a continuation of International application No. PCT/JP2018/000515 filed on Jan. 11, 2018 and designated the U.S., the entire contents of which are incorporated herein by reference.

BACKGROUND OF THE INVENTION

1. Field of the Invention

The present disclosure relates to an ultrasonic diagnostic apparatus and an ultrasonic diagnostic system.

2. Description of the Related Art

In the related art, an ultrasonic diagnostic apparatus is known in which ultrasonic waves are irradiated toward a subject, reflected waves from the subject are received, and an ultrasonic image is acquired. In recent years, the use of a mobile ultrasonic diagnostic apparatus equipped with a rechargeable battery has been increasing.

Such a mobile ultrasonic diagnostic apparatus that, for example, all of the elements for performing processing for acquiring an ultrasonic image are built into the ultrasonic diagnostic apparatus is known. In such a mobile ultrasonic diagnostic apparatus, power consumption is reduced as a result of, for example, the number of channels of a probe being reduced.

See the following documents, for example: Japanese Patent Application Laid-Open No. 2012-161555
Japanese Patent Application Laid-Open No. 2005-110934

SUMMARY

The described technique relates to an ultrasonic diagnostic apparatus comprising: a probe configured to transmit ultrasonic waves to a living body and receive ultrasonic waves reflected by the living body; and a processor configured to, in a moving image mode, cause ultrasonic image data based on ultrasonic waves received by a first subset of the total number of oscillators that the probe has to be output, and in a static image mode, cause ultrasonic image data based on ultrasonic waves received by a second subset of the total number of oscillators that the probe has to be output, wherein the number of oscillators used in the second subset is greater than the number of oscillators used in the first subset.

In step S603, when the predetermined interval elapses, the control unit 241 generates a coefficient signal S12 having the values of the coefficients S1-S8 set to "1", and sends the coefficient signal S12 to the AMP and ADC unit 243 and the digital signal processing unit 244 (step S604).

Subsequently, in step S605, the control unit 241 determines whether ultrasonic image data based on the signals output from the eight oscillators 232 has been output. The ultrasonic image data output here is ultrasonic image data corresponding to an ultrasonic image of a single page of a static image.

Figure 9:
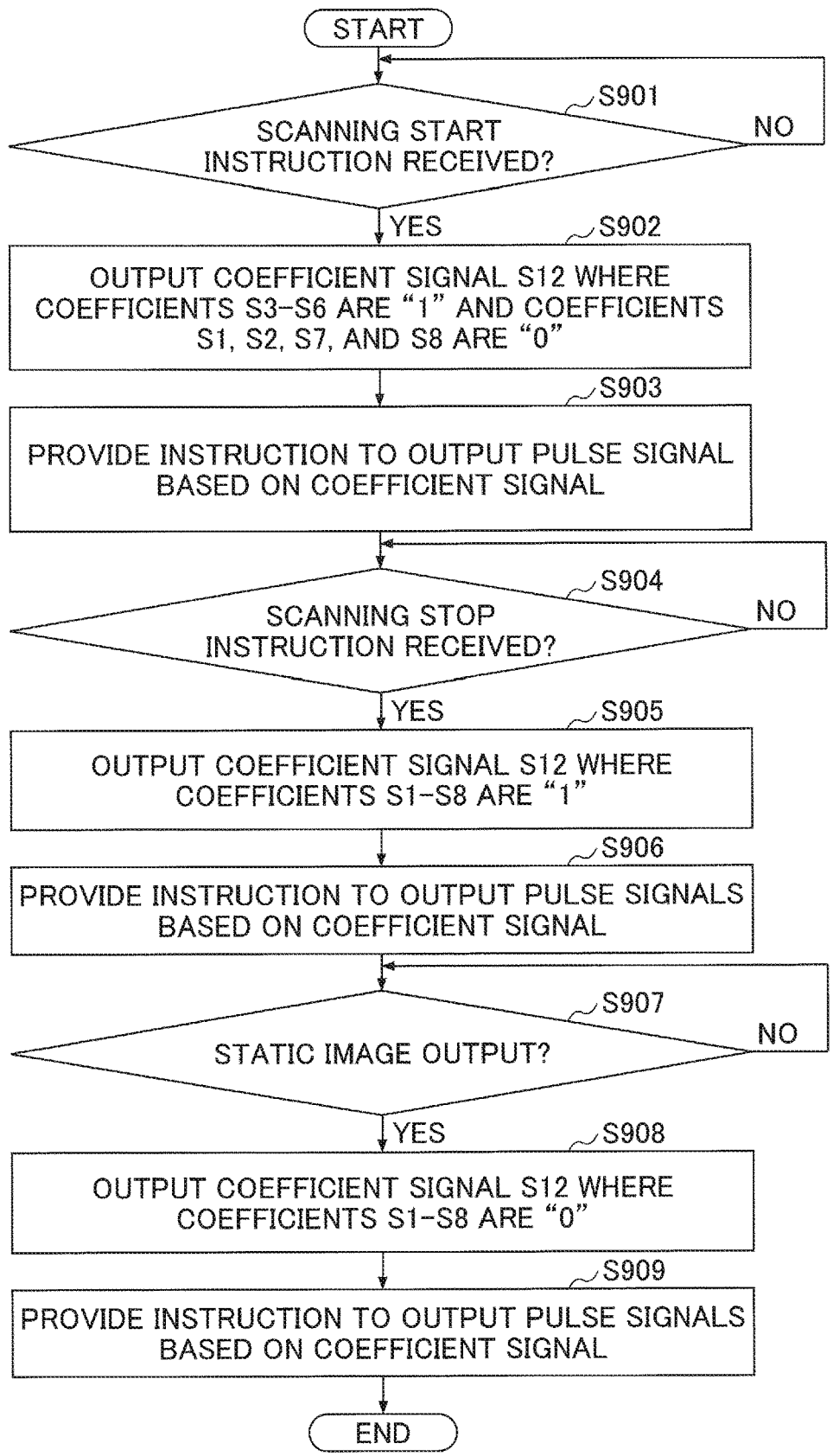
Figure 10:
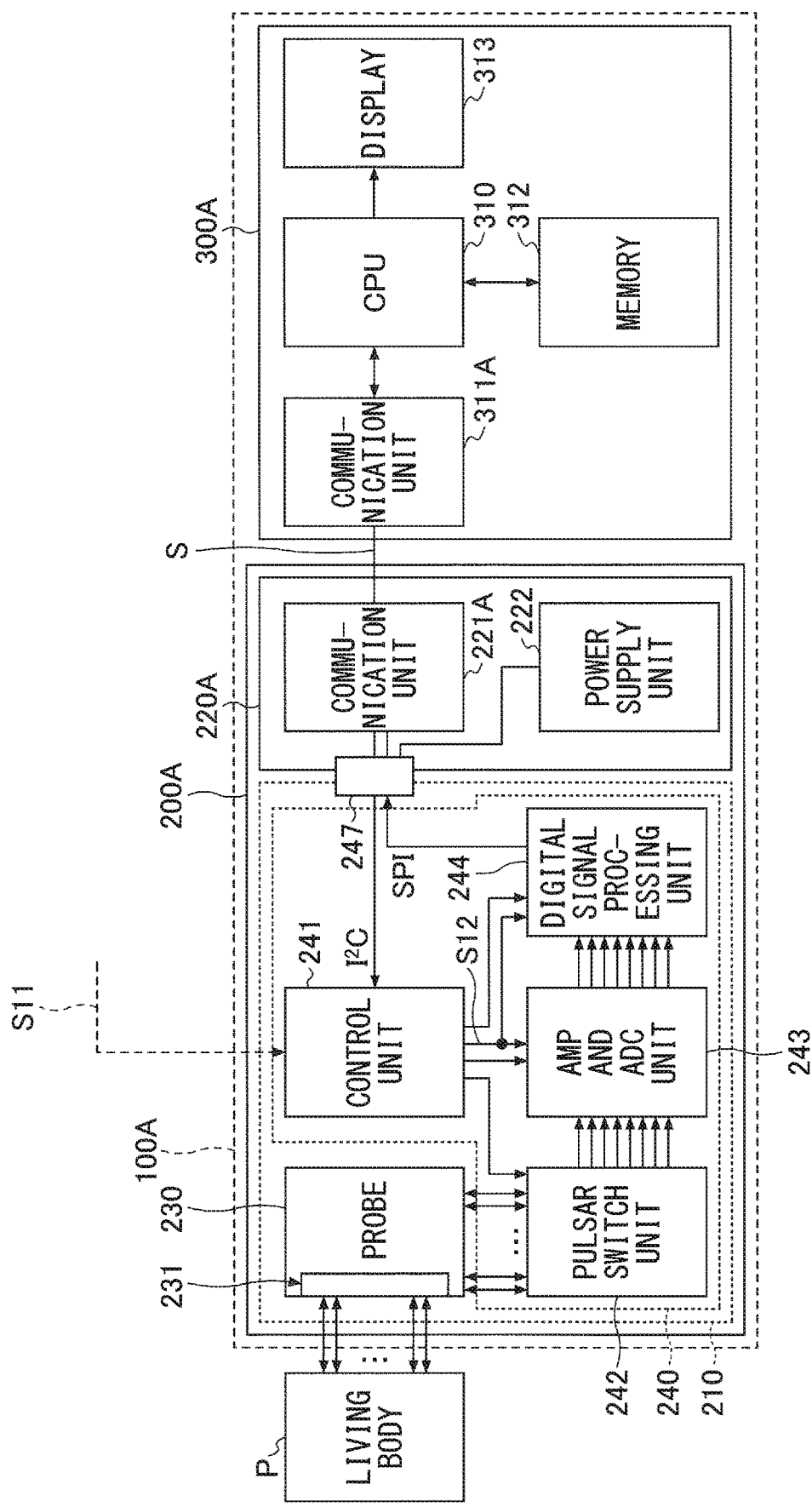
Figure 11:
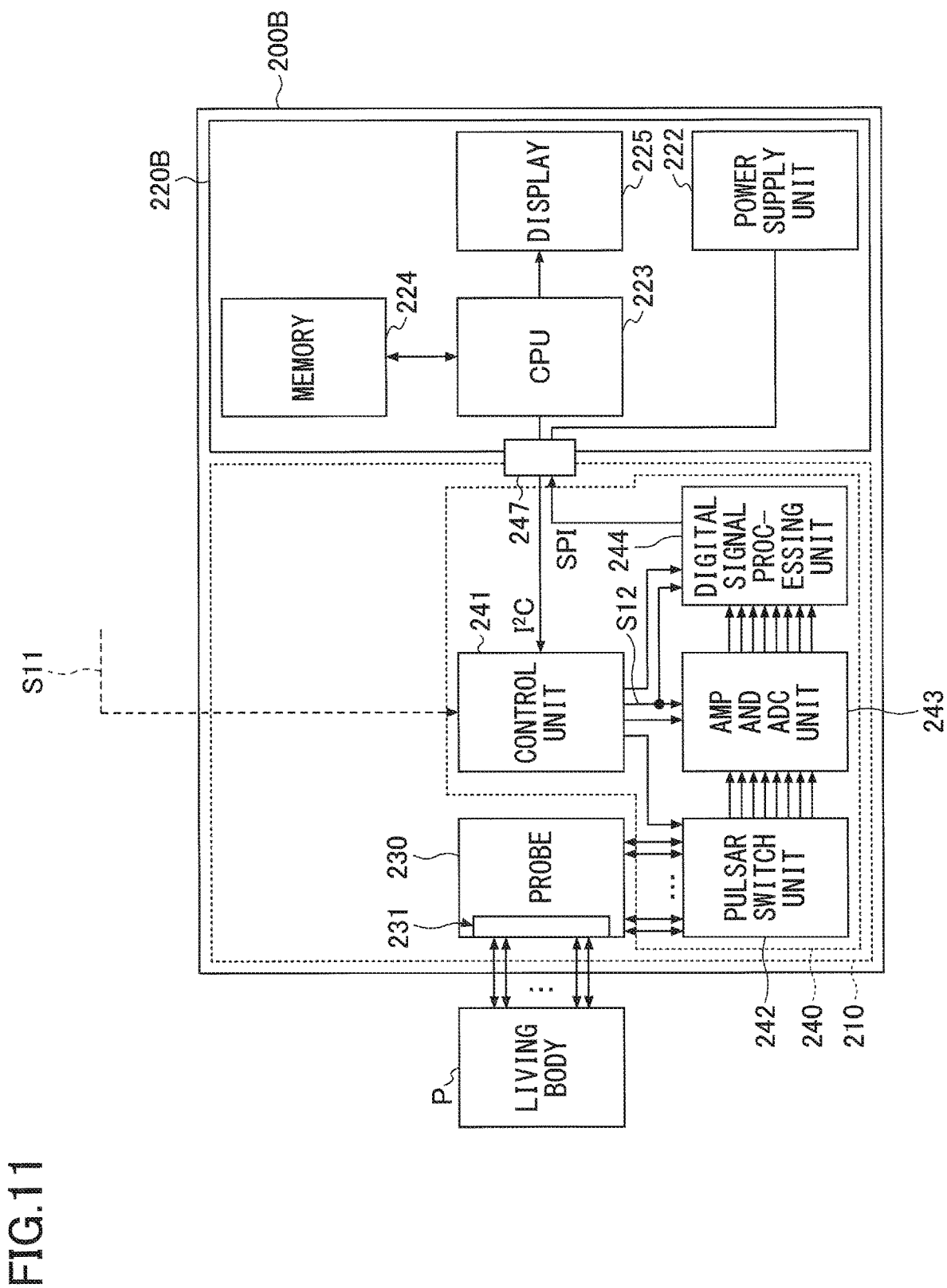

FIG. 9 is a flowchart illustrating operations of the control unit of an ultrasonic diagnostic apparatus according to the third embodiment;

FIG. 10 depicts the configuration of an ultrasonic diagnostic system according to a fourth embodiment; and FIG. 11 depicts the configuration of an ultrasonic diagnostic apparatus according to a fifth embodiment.

EMBODIMENTS OF THE INVENTION

Such an approach of the mobile ultrasonic diagnostic apparatus described above may result in degraded image quality of an ultrasonic image.

The described technology has been devised in light of the above circumstances, and is intended to reduce power consumption while maintaining image quality.

According to the described technology, it is possible to reduce power consumption while maintaining image quality.

First Embodiment

Figure 1:
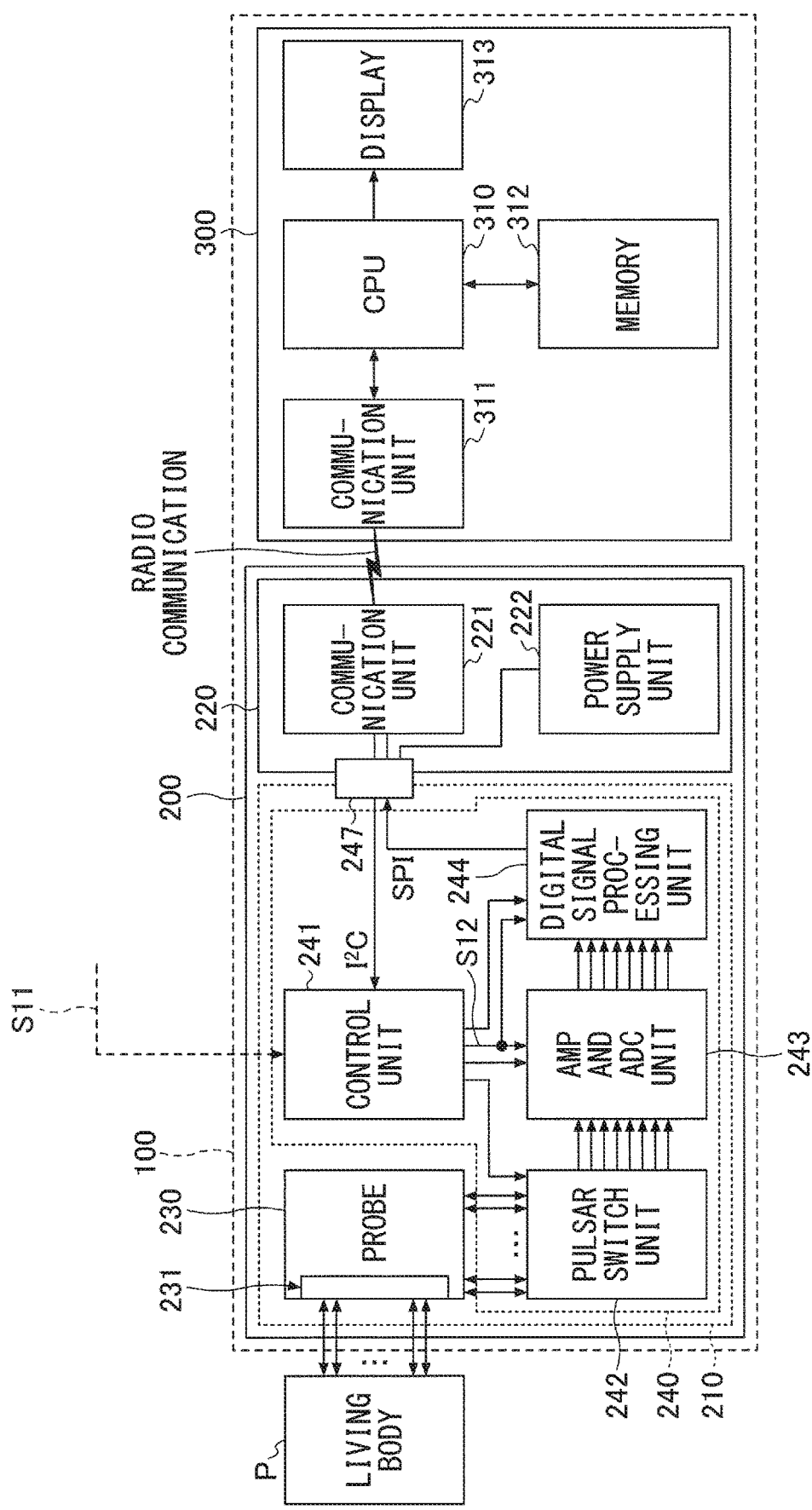
FIG. 1 depicts the configuration of an ultrasonic diagnostic system according to a first embodiment.

A first embodiment will now be described with reference to drawings. FIG. 1 is a diagram illustrating the configuration of an ultrasonic diagnostic system according to the first embodiment.

The ultrasonic diagnostic system 100 of the present embodiment includes an ultrasonic diagnostic apparatus 200 and a terminal apparatus 300. Radio communication is performed between the ultrasonic diagnostic apparatus 200 and the terminal apparatus 300.

First, the ultrasonic diagnostic apparatus 200 according to the present embodiment will be described. The ultrasonic diagnostic apparatus 200 of the present embodiment includes an ultrasonic image acquiring unit 210 including a probe 230 and a body unit 220.

The ultrasonic image acquiring unit 210 of the present embodiment includes the probe 230 and an image processing unit 240.

The probe 230 includes an oscillator array 231 including a plurality of oscillators arranged in an array. With respect to the probe 230 of the present embodiment, in the oscillator array 231, oscillators selected as transmitting apertures and receiving apertures are sequentially switched, transmit ultrasonic waves and receive ultrasonic waves reflected by a living body. Details of the probe 230 will be described below.

The image processing unit 240 includes a control unit 241, a pulsar switch unit 242, an amplifier (AMP) and analog-to-digital converter (ADC) unit 243, and a digital signal processing unit 244. The image processing unit 240 causes the probe 230 to transmit ultrasonic waves, generates ultrasonic image data based on reflected waves (ultrasonic waves) received by the probe 230, and outputs ultrasonic image data to the body unit 220.

The control unit 241 controls the whole ultrasonic diagnostic apparatus 200. The control unit 241 is connected to a connector 247 by I-squared-C (I²C) or the like. A signal output from the body unit 220 is input to the control unit 241 through the connector 247.

The control unit 241 according to the present embodiment changes the number of channels that convert analog signals into digital signals in the AMP and ADC unit 243 in response to an operator's operation to start measurement or stop measurement to the ultrasonic diagnostic apparatus 200. Details of the control unit 241 will be described later The pulsar switch unit 242 selects the probe 230 by a switch unit and transmits pulse signals to the probe 230 to cause the probe 230 to irradiate a living body P with ultrasonic waves.

When ultrasonic waves are emitted, the living body P reflects the ultrasonic waves at boundaries with respect to different acoustic impedances. The reflected waves reflected by the living body P are received by the probe 230 and are output to the AMP and ADC unit 243 selected by a switch unit of the pulsar switch unit 242.

The AMP and ADC unit 243 amplifies the reflected ultrasonic waves output from the pulsar switch unit 242 by an amplifier (AMP), converts the reflected waves into digital signals by an ADC, and outputs the digital signals to the digital signal processing unit 244.

The digital signal processing unit 244 performs various processes on the digital signals output from the AMP and ADC unit 243, acquires ultrasonic image data, and outputs the ultrasonic image data to the body unit 220 through the connector 247.

In more detail, the processes performed by the digital signal processing unit 244 include a process for aligning delays from times when the reflected waves are output from the pulsar switch unit 242, an averaging (phasing addition) process, a gain correction process taking into account attenuation in the living body P, and an envelope process for retrieving brightness information.

The digital signal processing unit 244 is connected to the connector 247 by a serial peripheral interface (SPI) or the like, and transmits ultrasonic image data to the body unit 220 through the SPI.

The body unit 220 according to the present embodiment includes a communication unit 221 and a power supply unit 222, and is connected to the ultrasonic image acquiring unit 210 through the connector 247.

The communication unit 221 communicates with the terminal apparatus 300. In more detail, the communication unit 221 performs, for example, radio communication with the terminal apparatus 300 in accordance with a standard such as Wi-Fi. The standard used for the radio communication is not limited to Wi-Fi and may be another standard.

The communication unit 221 is connected with the connector 247 and receives a signal transmitted from the terminal apparatus 300. In more detail, the communication unit 221 receives, for example, an ultrasonic emission instruction or the like from the terminal apparatus 300.

The communication unit 221 according to the present embodiment transmits a signal output from the ultrasonic image acquiring unit 210 to the terminal apparatus 300. In more detail, the communication unit 221 transmits ultrasonic image data to the terminal apparatus 300.

The power supply unit 222 may be, for example, a rechargeable secondary battery or the like to supply power to each unit of the ultrasonic diagnostic apparatus 200.

Thus, in the ultrasonic diagnostic apparatus 200 of the present embodiment, the ultrasonic image acquiring unit 210 digitizes ultrasonic image data and then outputs digital signals to the body unit 220. In other words, according to the present embodiment, ultrasonic image data to be transferred between the ultrasonic image acquiring unit 210 and the body unit 220 is digital signals (digital data).

Next, the terminal apparatus 300 according to the present embodiment will be described. The terminal apparatus 300 according to the present embodiment includes a CPU 310, a communication unit 311, a memory 312, and a display 313.

The CPU 310 controls operations of the whole terminal apparatus 300. The communication unit 311 receives a signal transmitted from the ultrasonic diagnostic apparatus 200. In more detail, the communication unit 311 receives ultrasonic image data transmitted from the ultrasonic diagnostic apparatus 200.

The memory 312 stores ultrasonic image data received by the communication unit 311 and data obtained as a result of calculation by the CPU 310.

The display 313 displays, for example, ultrasonic image data received from the ultrasonic diagnostic apparatus 200. Here, the ultrasonic image data displayed on the display 313 is ultrasonic image data of a moving image acquired during scanning of the living body P by the ultrasonic diagnostic apparatus 200 or ultrasonic image data of a static image acquired when the scanning of the living body P by the ultrasonic diagnostic apparatus 200 has been stopped.

The terminal apparatus 300 according to the present embodiment may be, for example, a tablet type terminal apparatus, and in this case, the display 313 includes a touch panel, for example.

In the ultrasonic diagnostic system 100 according to the present embodiment, ultrasonic image data is transmitted from the ultrasonic diagnostic apparatus 200 to the terminal apparatus 300 by radio communication. Accordingly, according to the present embodiment, when the ultrasonic diagnostic apparatus 200 scans the living body P, an operation of the operator of the ultrasonic diagnostic apparatus 200 is not limited by a communication cable or the like.

Figure 2:
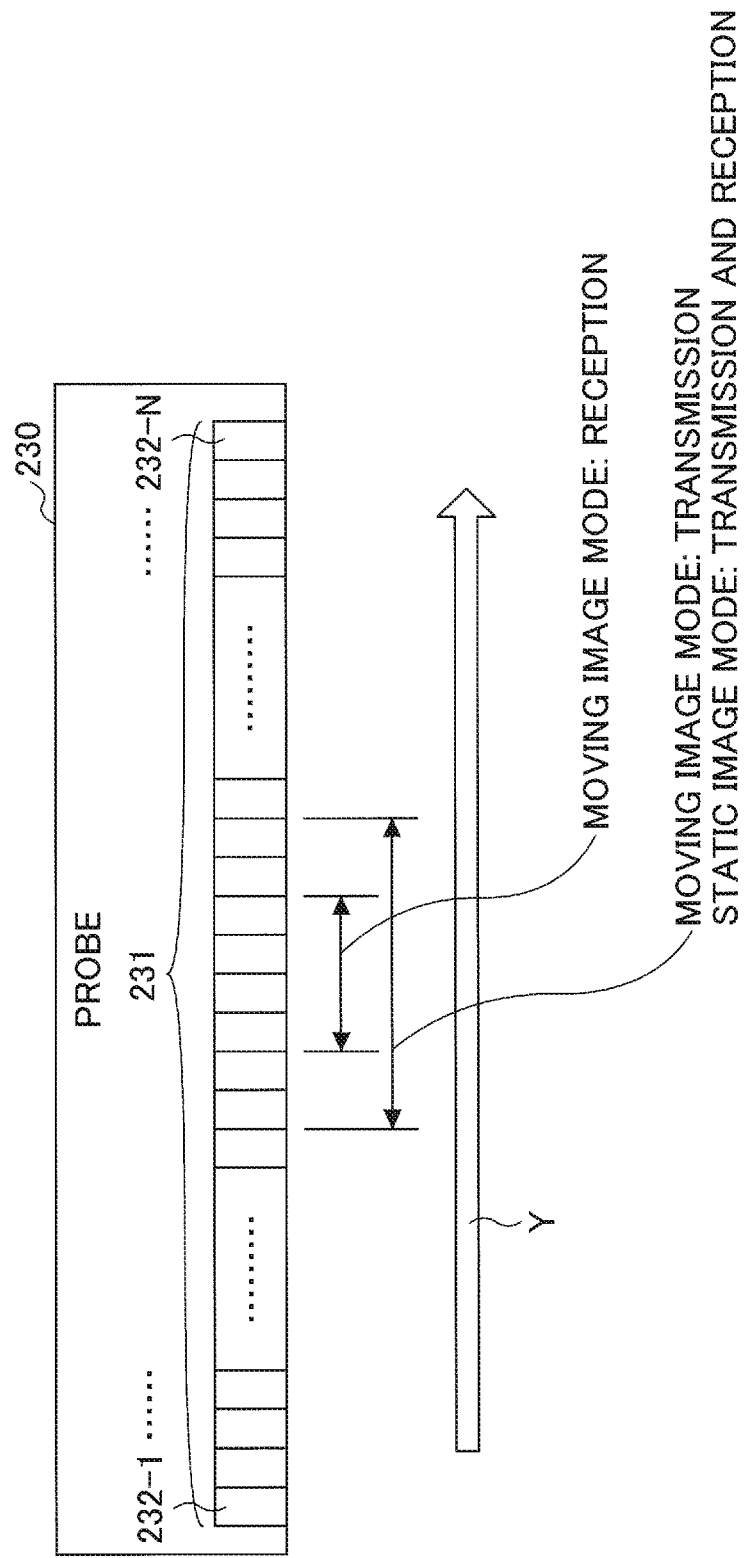
FIG. 2 depicts a probe according to the first embodiment.

Next, the probe 230 of the present embodiment will be described with reference to FIG. 2. FIG. 2 is a diagram illustrating the probe according to the first embodiment.

The probe 230 in the present embodiment includes the oscillator array 231. The oscillator array 231 includes N oscillators 232-1 to 232-N arranged in a single row.

In the present embodiment, oscillators 232 to be used as transmitting apertures and receiving apertures are sequentially selected to move the transmitting apertures and the receiving apertures over the oscillator array 231 to implement scanning of the living body P with ultrasonic waves.

In more detail, for example, in the probe 230, in the direction of the arrow Y, first, a predetermined number of oscillators 232 may be selected starting from the first oscillator 232-1 depicted on the left side of FIG. 2 as transmitting apertures and receiving apertures. Then, the predetermined number of oscillators 232 may instead be selected starting from a subsequent oscillator, such as the second oscillator 232-2, the third oscillator 232-3, and so on as transmitting apertures and receiving apertures. In this way, finally, the predetermined number of oscillators 232 may be selected ending at the last oscillator 232-N depicted on the right side of FIG. 2.

In the probe 230 of the present embodiment, oscillators 232 are used as transmitting apertures also are used as receiving apertures. That is, in the present embodiment, when oscillators 232 used as transmitting apertures output ultrasonic waves, the same oscillators 232 receive reflected waves as receiving apertures and output signals generated based on the reflected waves.

In the ultrasonic diagnostic apparatus 200 of the present embodiment, during scanning of the living body P by the probe 230, an ultrasonic image is acquired based on some of the signals output from oscillators 232 used as receiving apertures. Also, in the present embodiment, after scanning of the living body P by the probe 230 is stopped, an ultrasonic image based on the signals output from all the oscillators 232 that are used as receiving apertures is acquired.

During scanning of the living body P by the probe 230, an ultrasonic image output from the ultrasonic diagnostic apparatus 200 is a moving image according to the scanning. After the scanning of the living body P by the probe 230 is stopped, an ultrasonic image output from the ultrasonic diagnostic apparatus 200 is a static image.

Therefore, in the following description, a mode of operation of the ultrasonic diagnostic apparatus 200 while the probe 230 is scanning the living body P is referred to as a moving image mode, and a mode of operation of the ultrasonic diagnostic apparatus 200 when the probe 230 has stopped the scanning the living body P is referred to as a static image mode.

Further, in the following description, acquiring an ultrasonic image (a moving image) by the ultrasonic diagnostic apparatus 200 in a moving image mode is synonymous with scanning the living body P with ultrasonic waves, and acquiring an ultrasonic image (a static image) by the ultrasonic diagnostic apparatus 200 in a static image mode is synonymous with stopping the scanning (measurement) of the living body P.

In the present embodiment, in a moving image mode, an ultrasonic image is acquired based on signals generated by a first subset of oscillators 232 of the total number of oscillators 232 used as receiving apertures. The number of oscillators used in the first subset of oscillators is less than the number of the oscillators 232 used in a second subset, which is used as receiving apertures, in a static image mode.

In more detail, for example, in the present embodiment, the number of oscillators used in the first subset in a moving image mode is set to four, and the number of oscillators used in the second subset in a static image mode is set to eight.

Thus, in the present embodiment, image quality of an ultrasonic image acquired in a static image mode is maintained and power consumption upon operation in a moving image mode can be reduced, by selecting of signals to be used for generating an ultrasonic image from among the signals output from the oscillators 232 that are used as receiving apertures, depending on the mode of operation.

In the present embodiment, in both a moving image mode and a static image mode, the number of oscillators 232 used as transmitting apertures and receiving apertures is 8.

In the present embodiment, in a moving image mode, from among the oscillators 232 used as transmitting apertures and receiving apertures, the signals output from four oscillators 232 arranged at a center are selected.

Next, the control unit 241, the AMP and ADC unit 243, and the digital signal processing unit 244 will be described with reference to FIG. 3.

Figure 3:
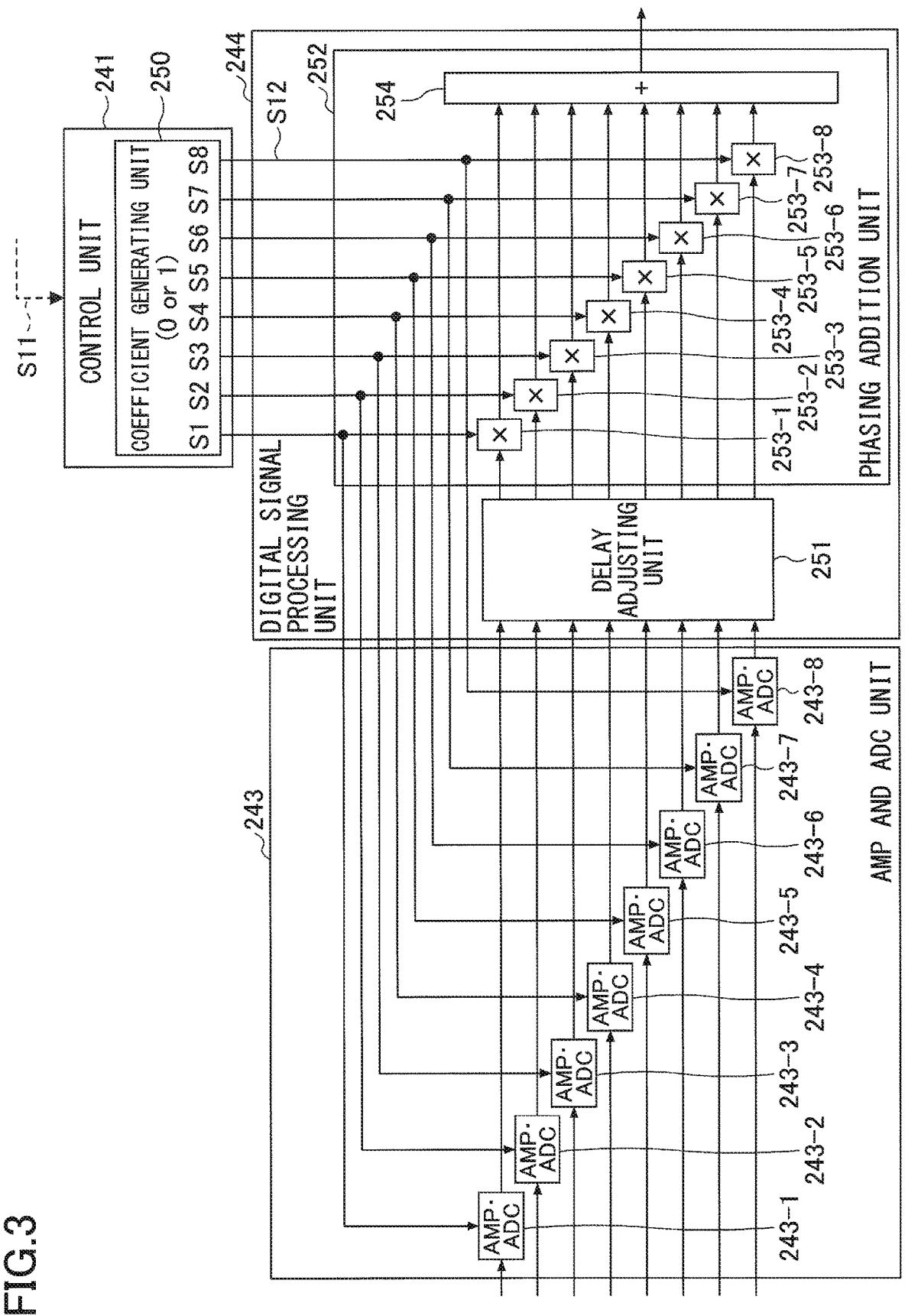
FIG. 3 depicts a control unit, an amplifier (AMP) and an analog-to-digital converter (ADC) unit, and a digital signal processing unit according to the first embodiment.

FIG. 3 is a diagram illustrating the control unit, the AMP and ADC unit, and the digital signal processing unit according to the first embodiment.

The control unit 241 according to the present embodiment includes a coefficient generating unit 250. The control unit 241 generates a coefficient signal S12 for selecting signals generated by oscillators 232 used as receiving apertures by the coefficient generating unit 250 based on a signal S11 indicating a start or a stop of scanning, and outputs the coefficient signal S12 to the AMP and ADC unit 243 and the digital signal processing unit 244.

The coefficient signal S12 is a binary signal and includes coefficients S1-S8 that designate the oscillators 232 to be used as transmitting apertures and receiving apertures. In the present embodiment, the number of oscillators 232 used as transmitting apertures and receiving apertures is 8.

The coefficients S1 and S8 correspond to both ends of the eight oscillators 232 selected as transmitting apertures and receiving apertures, and the coefficients S4 and S5 correspond to the oscillators 232 located at the center of the arrangement of the selected oscillators 232.

The AMP and ADC unit 243 includes an AMP and ADC element 243-1 through an AMP and ADC element 243-8 corresponding to the coefficients S1-S8 of the coefficient signal S12, and the values of the coefficients S1-S8 are input to the AMP and ADC elements 243-1 to 243-8, respectively.

In the present embodiment, the AMP and ADC unit 243 supplies power to the AMP and ADC elements 243-$n$ corresponding to the coefficients Sn having the values "1", which then amplify the signals output from the corresponding oscillators 232, convert the signals into digital signals, and output the digital signals to the digital signal processing unit 244.

In the present embodiment, power is not supplied to the AMP and ADC elements 243-$n$ corresponding to the coefficients Sn having the values "0". Accordingly, the signals output from the oscillators 232 corresponding to the coefficients Sn having the values "0" are invalidated.

That is, in the present embodiment, the signals output from the oscillators 232 corresponding to the coefficients Sn having the value "1" are selected from among the coefficients S1-S8 to generate an ultrasonic image.

The digital signal processing unit 244 includes a delay adjusting unit 251 and a phasing addition unit 252. The delay adjusting unit 251 synchronizes ultrasonic image data converted into digital signals by the AMP and ADC unit 243.

The phasing addition unit 252 includes multipliers 253-1 to 253-8 corresponding the coefficients S1-S8 of the coefficient signal S12, and an adder 254. The multipliers 253-1 to 253-8 multiply the signals output from the delay adjusting unit 251 by the coefficients Sn corresponding to the multipliers 253-$n$. The adder 254 adds the results multiplied by the multipliers 253-$n$.

Actually, in the digital signal processing unit 244, the values output from the AMP and ADC unit 243 are input to the multipliers 253-$n$ corresponding to the coefficients Sn having the value "1" and are multiplied by the corresponding coefficients Sn. In contrast, in the digital signal processing unit 244, the signals from the AMP and ADC unit 243 are not input to the multipliers 253-$n$ corresponding to the coefficients Sn having the values "0" and are therefore invalidated.

Accordingly, in the present embodiment, the ultrasonic image data generated based on the signals output from the oscillators 232 corresponding to the coefficients Sn having the values "1" in the coefficient signal S12 is output.

When the signal S11 indicates a start of scanning, a moving image mode starts, and therefore, the control unit 241 according to the present embodiment generates the coefficient signal S12, where four coefficients from among the coefficients S1-S8 are set to "1", and outputs the coefficient signal S12 to the AMP and ADC unit 243 and the digital signal processing unit 244.

In this regard, in the present embodiment, it is preferable that the coefficients Sn corresponding to oscillators 232 located at the center of the eight oscillators 232 have the values "1". In more detail, it is preferable that the coefficients S3-S6 be set to "1", and the coefficients S1, S2, S7, and S8 be set to "0".

When the coefficient signal S12 is input, only the AMP and ADC elements 243-3 to 243-6 are supplied with power, converts the signals input from the pulsar switch unit 242 into digital signals, and outputs the digital signal to the digital signal processing unit 244.

In the digital signal processing unit 244, the values "1" are input to the multipliers 253-3 to 253-6, and the values "0" are input to the other multipliers.

The adder 254 then adds the results of multiplication performed by the multipliers 253-3 to 253-6 and outputs the adding result as ultrasonic image data. That is, the ultrasonic image data is output based on the signals output from the four oscillators 232.

When the signal S11 indicates to stop scanning, a static image mode starts, and therefore, the control unit 241 generates the coefficient signal S12, where all of the coefficients S1-S8 are set to "1", and outputs the coefficient signal S12 to the AMP and ADC unit 243 and the digital signal processing unit 244.

When the coefficient signal S12 is input, the AMP and ADC unit 243 supply power to the AMP and ADC elements 243-1 to 243-8. The AMP and ADC elements 243-1 to 243-8 convert the signals input from the pulsar switch unit 242 into digital signals and output the digital signals to the digital signal processing unit 244.

In the digital signal processing unit 244, the values "1" are input to the multipliers 253-1 to 253-8. The adder 254 then adds the results of multiplication performed by the multipliers 253-1 to 253-8 and outputs the adding result as ultrasonic image data. That is, the ultrasonic image data is output based on the signals output from the eight oscillators 232.

After generating the coefficient signal S12, where all of the coefficients S1-S8 are set to "1", the control unit 241 of the present embodiment generates and outputs the coefficient signal S12, wherein all of the coefficients S1-S8 are set to "0."

The AMP and ADC unit 243 stops the supply of power to the AMP and ADC elements 243-1 to 243-8 when the coefficient signal S12, where all of the coefficients S1-S8 have the values "0", is input to the AMP and ADC unit 243. Therefore, digital signals are not output from the AMP and ADC unit 243. That is, in the present embodiment, ultrasonic image data is not acquired after the ultrasonic diagnostic apparatus 200 has been set to a static image mode.

Thus, according to the present embodiment, an ultrasonic image is acquired based on the signals output from eight oscillators 232 only when scanning of the living body P by the ultrasonic diagnostic apparatus 200 is stopped and an ultrasonic image is acquired. In this regard, "eight" is the number of oscillators used in the second subset. Therefore, according to the present embodiment, the image quality of an ultrasonic image of a static image can be improved compared to an ultrasonic image during scanning.

According to the present embodiment, in a moving image mode, ultrasonic image data is acquired based on the signals output from the four oscillators 232 arranged at the center of the oscillators 232 used as transmitting apertures and receiving apertures. Therefore, according to the present embodiment, the signals output from the oscillators 232 that receive the ultrasonic waves (reflected wave) having the high signal levels are selected, and a relatively satisfactory ultrasonic image can be acquired even in a moving image mode.

In addition, in the present embodiment, only four AMP and ADC units 243 are operated during scanning of the ultrasonic diagnostic apparatus 200, so that power consumption can be reduced.

Furthermore, according to the present embodiment, while an ultrasonic image is being viewed by a physician or the like after scanning by the ultrasonic diagnostic apparatus 200 is stopped, a new ultrasonic image is not acquired, and thus, power consumption can be reduced.

Figure 4:
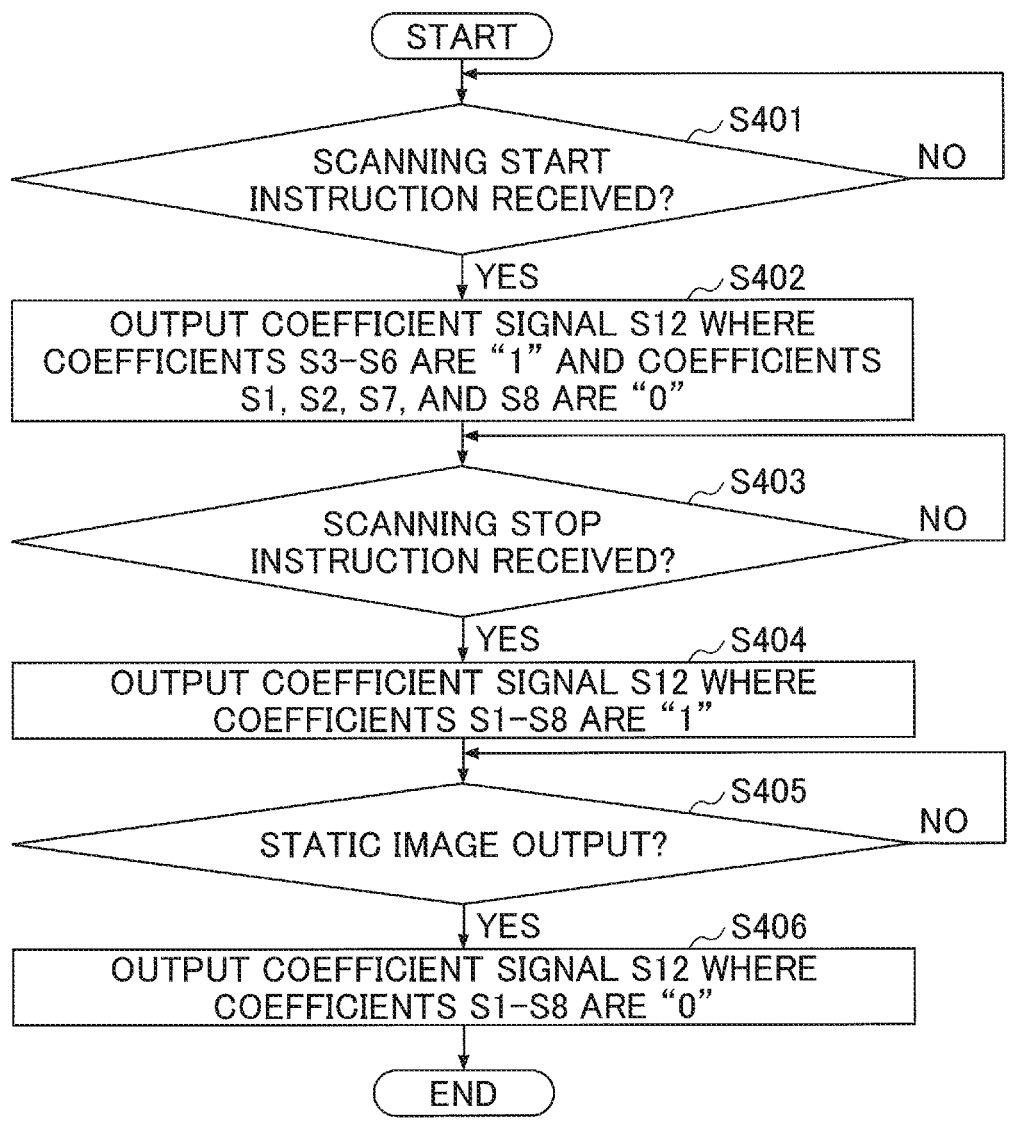
FIG. 4 is a flowchart illustrating operations of the control unit of the ultrasonic diagnostic apparatus according to the first embodiment.

In other words, the ultrasonic diagnostic apparatus 200 according to the present embodiment outputs ultrasonic image data acquired based on the ultrasonic signals received by the first subset of the total number of oscillators that the probe 230 has to the terminal apparatus 300 during scanning of a living body. Then, the ultrasonic diagnostic apparatus 200 according to the present embodiment outputs ultrasonic image data acquired based on the ultrasonic signals received by the second subset of oscillators of the total number of oscillators that the probe 230 has to the terminal apparatus 300 after the end of scanning of the living body. In this regard, the number of oscillators used in the second subset is greater than the number of oscillators used in the first subset, Hereinafter, operations of the control unit 241 according to the present embodiment will be further described with reference to FIGS. 4 and 5. FIG. 4 is a flowchart illustrating operations of the control unit of the ultrasonic diagnostic apparatus according to the first embodiment.

In step S401, the control unit 241 of the present embodiment determines whether an instruction to start scanning a subject with ultrasonic waves has been received. In other words, the control unit 241 of the present embodiment determines whether the signal S11 indicates to start scanning.

The ultrasonic diagnostic apparatus 200 may have, for example, a button or the like on a housing for an operator to input an instruction to start or stop scanning. Each time such a button is pressed, the signal S11 representing start or stop of scanning may be input to the control unit 241.

In step S401, when an instruction to start scanning is not received, the control unit 241 waits until such an instruction is received.

In step S401, when an instruction to start scanning is received, the control unit 241 generates the coefficient signal S12, where the values of the coefficients S3-S6 are set to "1" and the values of the coefficients S1, S2, S7, and S8 are set to "0", by the coefficient generating unit 250, and outputs the coefficient signal S12 to the AMP and ADC unit 243 and the digital signal processing unit 244 (step S402).

Subsequently, in step S403, the control unit 241 determines whether an instruction to stop scanning is received. In other words, the control unit 241 determines whether the signal S11 representing to stop scanning has been input.

In step S403, when an instruction to stop scanning is not received, the control unit 241 waits until such an instruction is received. In step S403, when an instruction to stop scanning is received, the control unit 241 generates the coefficient signal S12 having the values of the coefficients S1-S8 set to "1" by the coefficient generating unit 250 and outputs the coefficient signal S12 to the AMP and ADC unit 243 and the digital signal processing unit 244 (step S404).

Subsequently, in step S405, the control unit 241 determines whether ultrasonic image data of a static image has been output to the terminal apparatus 300. In step S405, when ultrasonic image data has not been output, the control unit 241 waits until ultrasonic image data is output.

In step S405, once ultrasonic image data has been output, the control unit 241 generates the coefficient signal S12 having the values of the coefficients S1-S8 set to "0" by the coefficient generating unit 250, outputs the coefficient signal S12 to the AMP and ADC unit 243 and the digital signal processing unit 244 (step S406), and ends the process.

Figure 5:
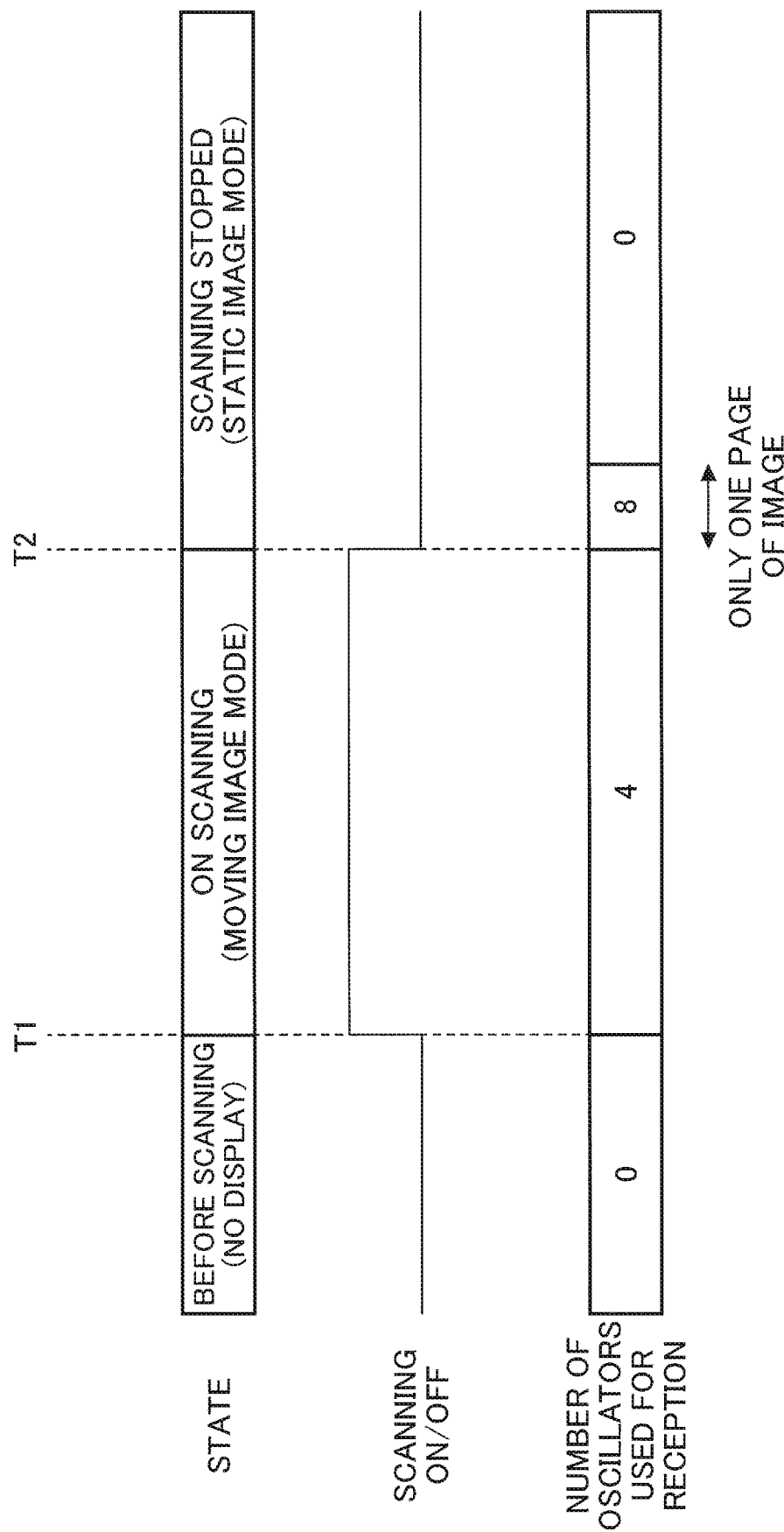
FIG. 5 is a timing chart illustrating operations of the ultrasonic diagnostic apparatus according to the first embodiment.

FIG. 5 is a timing chart illustrating operations of the ultrasonic diagnostic apparatus according to the first embodiment. FIG. 5 depicts states of the ultrasonic diagnostic system 100 and relationships between start or stop of scanning and the number of channels used.

In the ultrasonic diagnostic system 100 of the present embodiment, while scanning of a living body P with ultrasonic waves is not performed, ultrasonic waves are not transmitted, and the number of oscillators 232 used to receive reflected waves is zero.

In this state, when an instruction to start scanning of a living body P with ultrasonic waves is provided to the ultrasonic diagnostic apparatus 200 at a time T1, the state of the ultrasonic diagnostic system 100 is changed to a state of scanning (measuring). During scanning, the ultrasonic diagnostic apparatus 200 acquires ultrasonic image data in a moving image mode and displays the ultrasonic image data on the display 313 of the terminal apparatus 300. A moving image mode according to the present embodiment is a state starting from when the ultrasonic diagnostic system 100 receives an instruction to start scanning a living body P by the ultrasonic diagnostic apparatus 200 and ending when the ultrasonic diagnostic system 100 receives an instruction to stop scanning of the living body P.

At this time, the ultrasonic diagnostic apparatus 200 acquires ultrasonic image data based on the signals output from four oscillators 232.

Next, when an instruction to stop scanning is provided at a time T2, the ultrasonic diagnostic apparatus 200 outputs ultrasonic image data of a static image acquired based on the signals output from eight oscillators 232 to the terminal apparatus 300. The ultrasonic image data of the static image that is thus output is ultrasonic image data corresponding to a ultrasonic image of a single page of a static image.

A static image mode according to the present embodiment indicates a state where an ultrasonic image of a static image is displayed on the display 313 of the terminal apparatus 300 after an instruction to stop scanning of a living body P is received.

Then, the ultrasonic diagnostic apparatus 200 stops acquiring a ultrasonic image after acquiring the static image data.

At this time, the state of the ultrasonic diagnostic system 100 is a state where the acquired ultrasonic image data (the static image) is displayed on the display 313 of the terminal apparatus 300, and a state where acquisition of a new ultrasonic image has been stopped.

As described above, according to the present embodiment, power consumption can be reduced while maintaining the image quality of an ultrasonic image acquired as a static image.

In the present embodiment, the number of oscillators 232 used as transmitting apertures and receiving apertures is set to eight. However, the number of oscillators 232 used as transmitting apertures and receiving apertures is not limited to eight. For example, the number of oscillators 232 that are used as transmitting apertures and receiving apertures may be 32.

For example, in an ultrasonic diagnostic apparatus 200 having 32 oscillators 232 used as transmitting apertures and receiving apertures, when the signals output from eight oscillators 232 are used in a moving image mode, power consumption of the whole apparatus can be reduced from 2 W by approximately 0.75 W.

Second Embodiment

A second embodiment will now be described with reference to drawings. The second embodiment differs from the first embodiment in that, in a moving image mode, ultrasonic image data is acquired with the use of the signals output from eight oscillators 232 periodically. In the following description of the second embodiment, elements having functional configurations that are the same as or similar to the first embodiment are given the same reference signs, and the duplicate description is omitted.

In the present embodiment, the control unit 241 acquires ultrasonic image data based on the signals output from eight oscillators 232 at every predetermined time interval or at every predetermined frame of the ultrasonic image data acquired as a moving image during scanning of a living body P by the ultrasonic diagnostic apparatus 200 (in a moving image mode).

Figure 6:
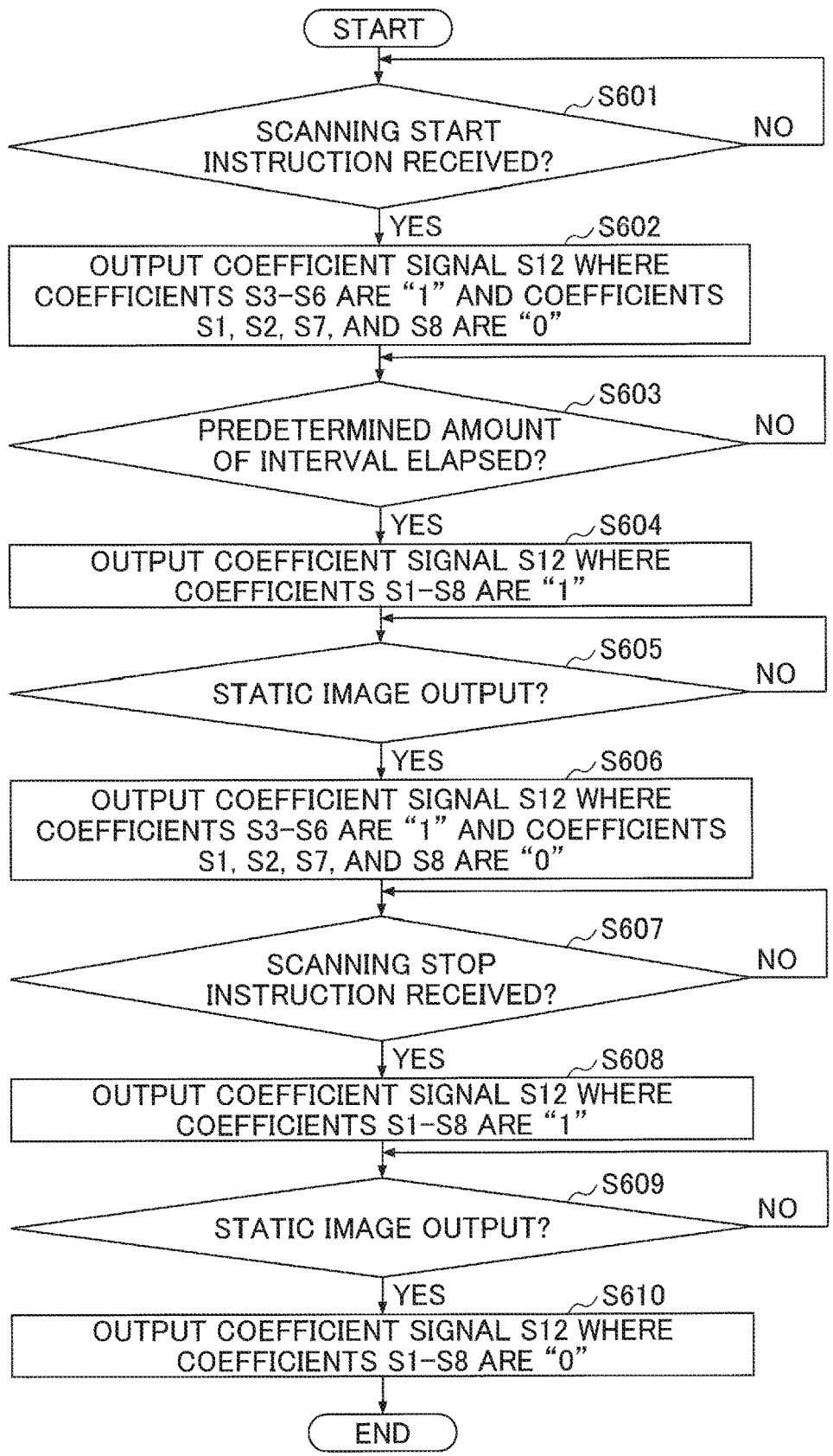
FIG. 6 is a flowchart illustrating operations of the control unit of an ultrasonic diagnostic apparatus according to a second embodiment.

FIG. 6 is a flowchart illustrating operations of the control unit of the ultrasonic diagnostic apparatus according to the second embodiment.

Because step S601 and step S602 in FIG. 6 are the same as step S401 and step S402 in FIG. 4, the description thereof will be omitted.

In step S602, the control unit 241 determines whether a predetermined interval (time) has elapsed. In step S603, when the predetermined interval has not elapsed, the control unit 241 waits until the predetermined interval has elapsed. The predetermined interval may be, for example, a time for acquiring 10 frames of ultrasonic image data.

In step S603, when the predetermined interval elapses, the control unit 241 generates a coefficient signal S12 having the values of the coefficients S1-S8 set to "1", and sends the coefficient signal S12 to the AMP and ADC unit 243 and the digital signal processing unit 244 (step S604).F Subsequently, in step S605, the control unit 241 determines whether ultrasonic image data based on the signals output from the eight oscillators 232 has been output. The ultrasonic image data output here Sis ultrasonic image data corresponding to an ultrasonic image of a single page of a static image.

In step S605, when the ultrasonic image data has not been output, the control unit 241 waits until the ultrasonic image data is output.

In step S605, when the ultrasonic image data is output, the control unit 241 proceeds to step S606.

Because steps S606-S610 are the same as steps S402-S406 of FIG. 4, the description thereof will be omitted.

In the present embodiment, even in a moving image mode, the signals output from eight oscillators 232 can be selected periodically so that high image quality ultrasonic image data can be acquired periodically, and thereby, it is possible to maintain the image quality of a moving image.

In this regard, in the operation procedure of FIG. 6, as a result of step S603 being performed instead of step S607 being repeated when an instruction to stop scanning has not been received in step S607, the signals output from eight oscillators 232 can be selected periodically a plurality of times even in a moving image mode so that high image quality ultrasonic image data can be acquired periodically a plurality of times.

Third Embodiment

A third embodiment will now be described with reference to drawings. The third embodiment differs from the first embodiment in that the number of oscillators 232 used as transmitting apertures and receiving apertures differs from the first embodiment in a moving image mode and in a static image mode. Accordingly, in the description of the third embodiment below, only the differences from the first embodiment are described, and elements having functional configurations that are the same as or similar to the first embodiment are given the same reference signs as those used in the description of the first embodiment, and the description thereof is omitted.

First, transmitting apertures in a moving image mode and in a static image mode will be described with reference to FIG. 7.

Figure 7:
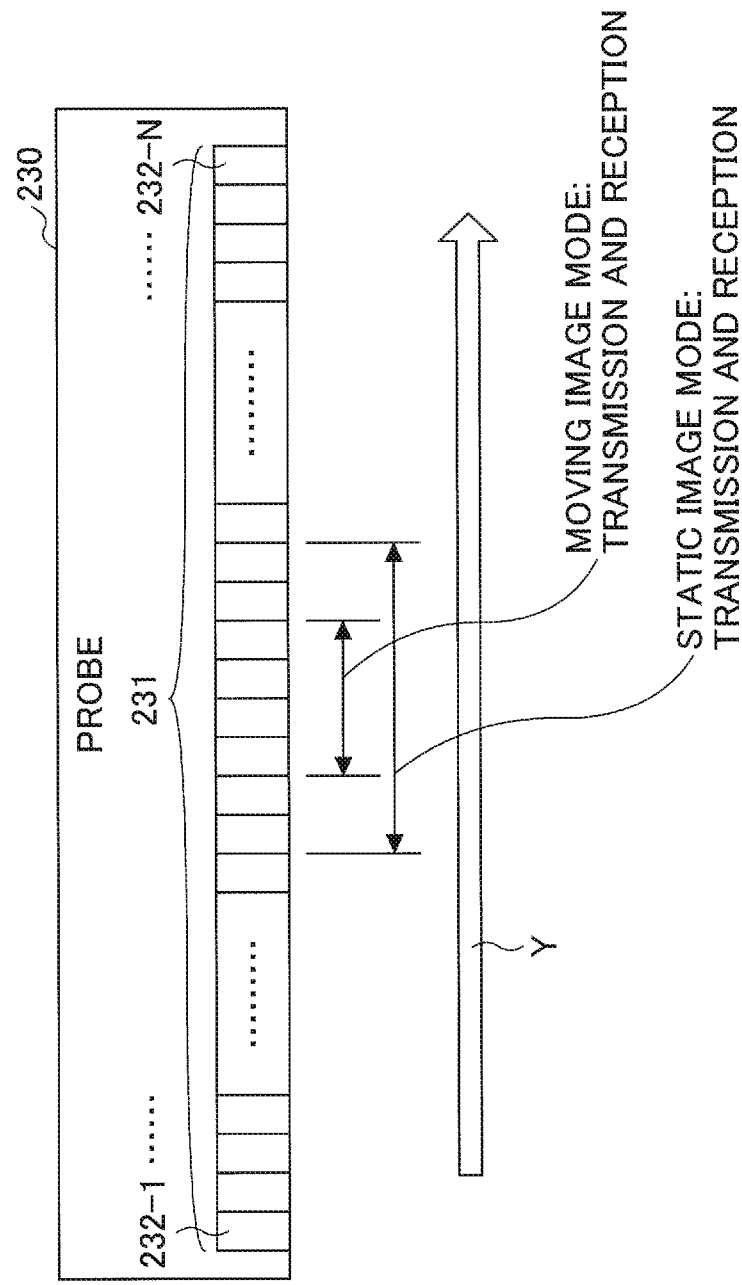

FIG. 7 is a diagram illustrating the probe according to the third embodiment. In the present embodiment, the number of oscillators 232 used as transmitting apertures and receiving apertures in a moving image mode is less than the number of oscillators 232 used as transmitting apertures and receiving apertures in a static image mode. In more detail, in the present embodiment, the number of oscillators 232 used as transmitting apertures and receiving apertures in a moving image mode is four.

Accordingly, in the present embodiment, the number of oscillators 232 to be driven in a moving image mode can be reduced to be smaller than the number of oscillators 232 to be driven in a static image mode, and thereby, it is possible to reduce the power consumption of the ultrasonic diagnostic apparatus in a moving image mode.

Figure 8:
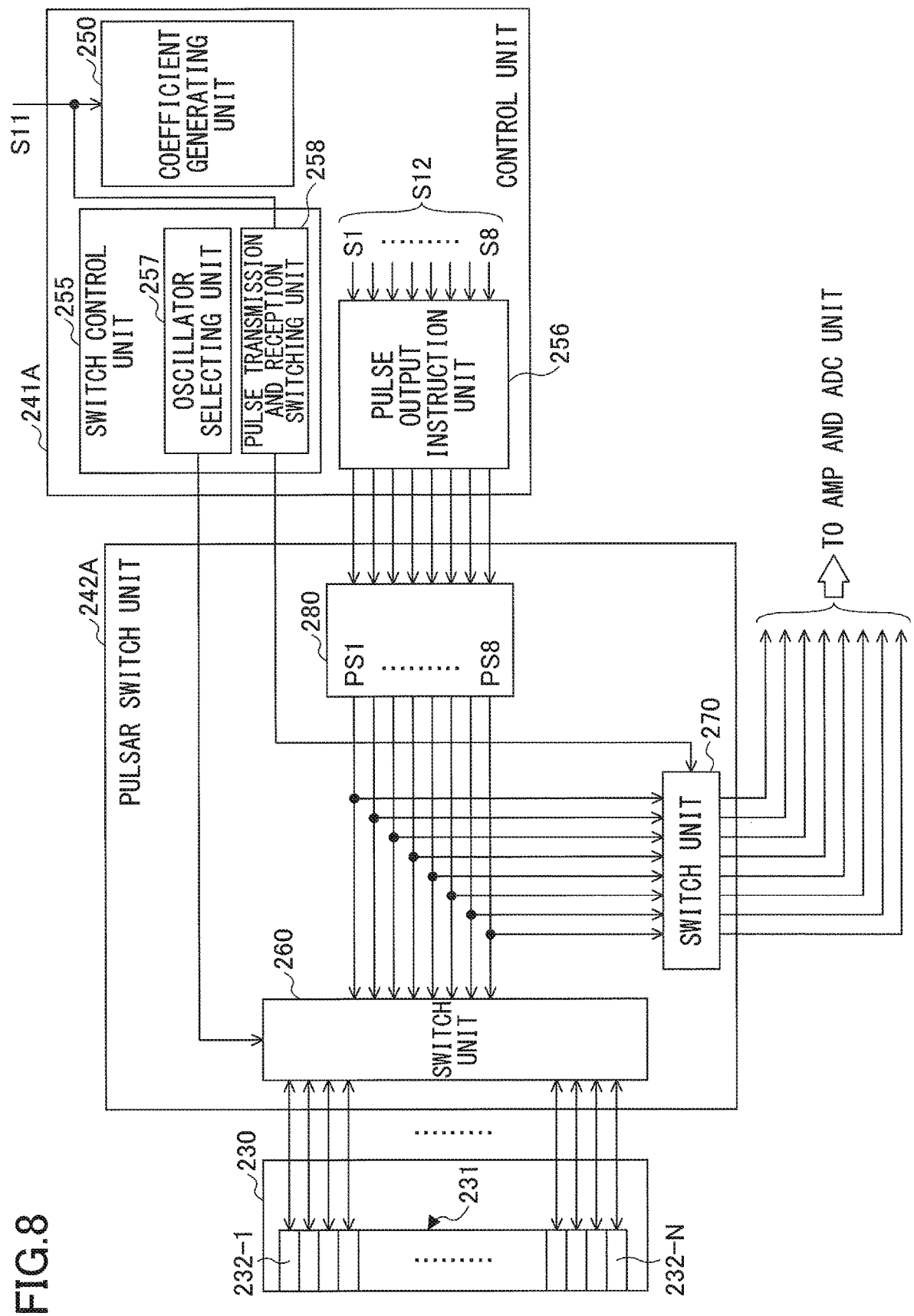

Next, a selection of oscillators 232 according to the present embodiment will be described with reference to FIG. 8. FIG. 8 is a diagram illustrating a control unit and a pulsar switch unit according to the third embodiment.

The control unit 241A according to the present embodiment includes a coefficient generating unit 250, a switch control unit 255, and a pulse output instruction unit 256.

The switch control unit 255 includes an oscillator selecting unit 257 and a pulse transmission and reception switching unit 258.

The pulsar switch unit 242A in the present embodiment also includes a switch unit 260, a switch unit 270, and a pulsar 280.

When a coefficient signal S12 is input from the coefficient generating unit 250, the pulse output instruction unit 256 outputs an instruction signal, for causing the pulsar 280 to output pulse signals, to the pulsar 280 in response to the coefficient signal S12.

The oscillator selecting unit 257 output a selection signal to the switch unit 260 for controlling the switch unit 260 to select oscillators 232 to which the pulse signals output from the pulsar 280 are to be output.

The pulse transmitting and receiving switching unit 258 controls the switch unit 270 of the pulsar switch unit 242A to switch between ultrasonic wave transmission from the probe 230 and ultrasonic wave reception by the probe 230.

The pulsar 280 has output terminals PS1-PS8 corresponding to the coefficients S1-S8 and outputs the pulse signals from the output terminals PS1-PS8 in response to the instruction signal output from the pulse output instruction unit 256.

The instruction signal output from the pulse output instruction unit 256 will now be described. The instruction signal according to the present embodiment is a signal for causing the pulse signals to be output from the output terminals PSn corresponding to the coefficients Sn having the values "1" from among the coefficients included in the coefficient signal S12 that is input to the pulse output instruction unit 256.

For example, in a moving image mode, the coefficients S3-S6 are "1". Therefore, in a moving image mode, the pulsar 280 outputs the pulse signals from the output terminals PS3-PS6 corresponding to the coefficients S3-S6. In a static image mode, the pulsar 280 outputs the pulse signals from the output terminals PS1-PS8 corresponding to the coefficients S1-S8.

That is, the instruction signal output from the pulse output instruction unit 256 according to the present embodiment is a signal for selecting, by the oscillator selecting unit 257, oscillators 232 to be used as transmitting apertures and receiving apertures, from among oscillators 232 selected from the oscillator array 231, according to a mode of operation.

The switch unit 260 selects oscillators 232 to be used as transmitting apertures and receiving apertures from the oscillator array 231 according to the selection signal output from the oscillator selecting unit 257. In more detail, in the present embodiment, the oscillator selecting unit 257 selects, for example, eight oscillators 232 and connects these oscillators 232 to the pulsar 280 by the switch unit 260.

In a moving image mode, the pulse output instruction unit 256 in the present embodiment outputs the instruction signal for further selecting four oscillators 232 from among the selected eight oscillators 232 to the pulsar 280. The pulsar 280 outputs the pulse signals from the output terminals PS3-PS6 to the four oscillators according to the instruction signal. In the probe 230, the four oscillators 232, to which the pulse signals are input, are used as transmitting apertures and receiving apertures to output ultrasonic waves and receive reflected waves.

In a static image mode, the pulse output instruction unit 256 according to the present embodiment outputs the instruction signal for selecting all of the selected eight oscillators 232 to the pulsar 280. The pulsar 280 outputs the pulse signals from the output terminals PS1-PS8 to the eight oscillators according to the instruction signal. In the probe 230, the eight oscillators 232, to which the pulse signals are input, are used as transmitting apertures and receiving apertures to output ultrasonic waves and receive reflected waves.

In the present embodiment, the oscillators 232, selected to be used as receiving apertures, generate the signals based on the received reflected ultrasonic waves and transmit the signals to the switch unit 270 via the switch unit 260.

The switch unit 260 moves transmitting apertures and receiving apertures on the oscillator array 231 by sequentially switching the corresponding oscillators, to which the pulse signals output from the pulsar 280 are transmitted, among the plurality of oscillators 232-1 through 232-N.

The switch unit 270 disconnects the AMP and ADC unit 243 from the oscillators 232 when the pulse signals are output from the pulsar 280 to the oscillators 232 via the switch unit 260.

The switch unit 270 connects the AMP and ADC unit 243 to the oscillators 232 when the signals generated based on the reflected waves are output from the oscillators 232.

The signals output from the oscillators 232 to be used as receiving apertures are transmitted to the AMP and ADC unit 243 through the switch unit 270.

Hereinafter, operations of the control unit 241A according to the present embodiment will be described with reference to FIG. 9. FIG. 9 is a flowchart illustrating operations of the control unit of the ultrasonic diagnostic apparatus according to the third embodiment.

In step S901, the control unit 241A of the present embodiment determines whether an instruction to start scanning of a living body P by ultrasonic waves is received for the ultrasonic diagnostic apparatus 200. In step S901, when such an instruction is not received, the control unit 241A waits until such an instruction is received.

In step S901, when an instruction to start scanning is received, the control unit 241A generates a coefficient signal S12, where the values of the coefficients S3-S6 are set to "1" and the values of the coefficients S1, S2, S7, and S8 are set to "0", by the coefficient generating unit 250, and outputs the coefficient signal S12 to the pulse output instruction unit 256, the AMP and ADC unit 243, and the digital signal processing unit 244 (step S902).

Subsequently, in step S903, the control unit 241A sends, from the pulse output instruction unit 256, an instruction to the pulsar 280 of the pulsar switch unit 242A to cause the pulsar 280 to output pulse signals based on the coefficient signal S12. In more detail, the pulse output instruction unit 256 outputs to the pulsar 280 an instruction signal that causes pulse signals to be output from the output terminals PS3-PS6.

Subsequently, in step S904, the control unit 241A determines whether an instruction to stop scanning is received. In step S904, when such an instruction is not received, the control unit 241A waits until such an instruction is received.

In step S904, when an instruction to stop scanning is received, the control unit 241A generates a coefficient signal S12 having the values of the coefficients S1-S8 set to "1" using the coefficient generating unit 250 and outputs the coefficient signal S12 to the pulse output instruction unit 256, the AMP and ADC unit 243, and the digital signal processing unit 244 (step S905).

Subsequently, in step S906, the control unit 241A sends, from the pulse output instruction unit 256, an instruction to the pulsar 280 of the pulsar switch unit 242A to cause the pulsar 280 to output pulse signals based on the coefficient signal S12. In more detail, the pulse output instruction unit 256 outputs to the pulsar 280 an instruction signal that causes the pulsar 280 to output pulse signals from the output terminals PS1-PS8.

Subsequently, in step S907, the control unit 241A determines whether ultrasonic image data of a static image has been output to the terminal apparatus 300. In step S907, when ultrasonic image data has not been output, the control unit 241A waits until ultrasonic image data is output.

In step S907, when ultrasonic image data is output, the control unit 241A generates a coefficient signal S12 having the values of the coefficients S1-S8 set to "0" using the coefficient generating unit 250 and outputs the coefficient signal S12 to the pulse output instruction unit 256, the AMP and ADC unit 243, and the digital signal processing unit 244 (step S908).

Subsequently, in step S909, the control unit 241A sends, from the pulse output instruction unit 256, an instruction to the pulsar 280 of the pulsar switch unit 242A to cause the pulsar 280 to output pulse signals based on the coefficient signal S12, and ends the process. In more detail, the pulse output instruction unit 256 outputs to the pulsar 280 an instruction signal that causes the pulsar 280 to stop outputting pulse signals from the output terminals PS1-PS8.

Thus, in the present embodiment, it is possible to further reduce the power consumption by selecting oscillators 232 to which pulse signals are output according to a coefficient signal S12. In other words, in the present embodiment, the power consumption can be further reduced by reducing the number of oscillators 232 that are to output ultrasonic waves in a moving image mode.

For example, when the present embodiment is applied to an ultrasonic diagnostic apparatus 200 where 32 oscillators 232 are selected by the oscillator selecting unit 257 and the number of oscillators 232 that are destinations of pulse signals is set to 8 in a moving image mode, the power consumption of the whole apparatus can be reduced from 2 W by approximately 1 W. In other words, in the present embodiment, by reducing the number of oscillators 232 to be driven in a moving image mode, the power consumption can be further reduced by approximately 0.25 W.

Fourth Example

A fourth embodiment will be described below with reference to drawings. An ultrasonic diagnostic system of the fourth embodiment differs from the first embodiment only in that communication between the ultrasonic diagnostic apparatus and the terminal apparatus is wired communication instead of radio communication. Accordingly, in the description of the fourth embodiment below, only the differences from the first embodiment are described, and elements having functional configurations that are the same as or similar to the first embodiment are given the same reference signs as those used in the description of the first embodiment, and the description thereof is omitted.

FIG. 10 is a diagram illustrating the configuration of the ultrasonic diagnostic system according to the fourth embodiment. The ultrasonic diagnostic system 100A according to the present embodiment includes an ultrasonic diagnostic apparatus 200A and a terminal apparatus 300A. In the ultrasonic diagnostic system 100A, communication between the ultrasonic diagnostic apparatus 200A and the terminal apparatus 300A is wired communication.

The ultrasonic diagnostic apparatus 200A according to the present embodiment includes an ultrasonic image acquiring unit 210 and a body unit 220A. The body unit 220A includes a communication unit 221A and a power supply unit 222.

The communication unit 221A of the present embodiment is connected with a connector 247 and transmits ultrasonic image data received from the ultrasonic image acquiring unit 210 to the terminal apparatus 300A through wired communication. The wired communication may use any type of a wired communication method applicable to the communication between the ultrasonic diagnostic apparatus 200A and the terminal apparatus 300A.

The terminal apparatus 300A according to the present embodiment includes a CPU 310, a communication unit 311A, a memory 312, and a display 313. The communication unit 311A of the present embodiment performs wired communication with the ultrasonic diagnostic apparatus 200A.

In the ultrasonic diagnostic system 100A according to the present embodiment, even when the ultrasonic diagnostic apparatus 200A and the terminal apparatus 300A perform wired communication, the same advantageous effects as in the first embodiment can be achieved.

Fifth Embodiment

A fifth embodiment will be described below with reference to drawings. A ultrasonic diagnostic apparatus of the fifth embodiment differs from the first embodiment in that the ultrasonic diagnostic apparatus includes a display. Accordingly, in the description of the fifth embodiment below, only the differences from the first embodiment are described, and elements having functional configurations that are the same as or similar to the first embodiment are given the same reference signs as those used in the description of the first embodiment, and the description thereof is omitted.

FIG. 11 is a diagram illustrating the configuration of an ultrasonic diagnostic apparatus according to the fifth embodiment. The ultrasonic diagnostic apparatus 200B according to the present embodiment includes an ultrasonic image acquiring unit 210 and a body unit 220B.

The body unit 220B according to the present embodiment includes a power supply unit 222, a CPU 223, a memory 224, and a display 225.

The CPU 223 controls operations of the body unit 220B. In more detail, the CPU 223 is connected to a connector 247 and ultrasonic image data output from the ultrasonic image acquiring unit 210 is input to the CPU 223. The CPU 223 may display ultrasonic image data on the display 225 when the ultrasonic image data is input.

The memory 224 stores ultrasonic image data acquired by the CPU 223 and data obtained as a result of an operation by the CPU 223.

The display 225 displays ultrasonic image data acquired by the CPU 223. The display 225 may also display a variety of information regarding operator's operations on the ultrasonic diagnostic apparatus 200B.

Thus, according to the present embodiment, because the display 225 is provided in the ultrasonic diagnostic apparatus 200B, ultrasonic image data can be displayed without communicating with the terminal apparatus 300. In other words, according to the present embodiment, the terminal apparatus 300 is not needed for displaying the ultrasonic image data.

Thus, the ultrasonic diagnostic apparatuses and the ultrasonic diagnostic systems have been described with reference to the embodiments. However, the present invention is not limited to the above-described embodiments. Various modifications and improvements may be made within the scope of the present invention.

All examples and conditional language recited herein are intended for pedagogical purposes to aid the reader in understanding the invention and the concepts contributed by the inventors to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An ultrasonic diagnostic apparatus, comprising:
a probe configured to transmit ultrasonic waves to a living body and receive ultrasonic waves reflected by the living body; and
a processor configured to:
in a moving image mode, cause ultrasonic image data based on ultrasonic waves received by a first subset of the total number of oscillators that the probe has, to be output, and
in a static image mode, cause ultrasonic image data based on ultrasonic waves received by a second subset of the total number of oscillators that the probe has, to be output, wherein the number of oscillators used in the second subset is greater than the number of oscillators used in the first subset,
wherein the processor is further configured to, in each of the static image mode and the moving image mode, cause oscillators to transmit ultrasonic waves, the number of the oscillators transmitting the ultrasonic waves being the same as the number of oscillators used in the second subset in each of the static image mode and the moving image mode.

2. The ultrasonic diagnostic apparatus as claimed in claim 1, wherein the processor is further configured to, after causing the ultrasonic image data to be output in the static image mode, stop outputting of the ultrasonic image data based on the ultrasonic waves received by the second subset of oscillators.

3. The ultrasonic diagnostic apparatus as claimed in claim 1, wherein the processor is further configured to:
in the moving image mode, cause oscillators, from among the total number of oscillators that the probe has, to transmit ultrasonic waves, the number of the oscillators caused to transmit the ultrasonic waves being the same as the number of oscillators used in the first subset, and
in the static image mode, cause oscillators, from among the total number of oscillators that the probe has, to transmit ultrasonic waves, the number of the oscillators caused to transmit the ultrasonic waves being the same as the number of oscillators used in the second subset.

4. The ultrasonic diagnostic apparatus as claimed in claim 1, wherein the first subset of oscillators is at a center of the second subset of oscillators with respect to a direction in which the second subset of oscillators selected from among the total number of oscillators is arranged.

5. The ultrasonic diagnostic apparatus as claimed in claim 1, wherein
the moving image mode denotes a state starting at receiving an instruction to start the probe's scanning of the living body and ending at receiving an instruction to stop the scanning, and
the static image mode denotes a state where, after the instruction to stop the scanning is received, the ultrasonic image data based on the ultrasonic waves received by the second subset of oscillators is displayed on a display.

6. The ultrasonic diagnostic apparatus as claimed in claim 1, further comprising:
an A/D converter configured to convert the ultrasonic waves received by the second subset of oscillators into a digital signal; and
a digital signal processor configured to perform signal processing on the digital signal output from the A/D converter, wherein
the processor is further configured to generate, using coefficients corresponding to the oscillators used in the second subset selected from among the total number of oscillators based on a signal indicating a start or a stop of scanning, a coefficient signal for causing signals output from the first subset of oscillators or signals output from the second subset of oscillators to be selected,
the processor is further configured to, in the moving image mode, output a coefficient signal for causing the signals output from the first subset of oscillators to the A/D converter and the digital signal processor to be selected, and the processor is further configured to, in the static image mode, output a coefficient signal for causing the signals output from the second subset of oscillators to the A/D converter and the digital signal processor to be selected.

7. The ultrasonic diagnostic apparatus as claimed in claim 1, wherein the processor is further configured to:
in the moving image mode, cause the ultrasonic image data on the basis of the ultrasonic waves received by the second subset of oscillators to be output at a predetermined interval.

8. An ultrasonic diagnostic apparatus, comprising:
a probe configured to transmit ultrasonic waves to a living body and receive ultrasonic waves reflected by the living body; and
a processor configured to:
cause ultrasonic image data based on ultrasonic waves received by a first subset of the total number of oscillators that the probe has, to be output, and
at a predetermined interval, cause ultrasonic image data based on ultrasonic waves received by a second subset of the total number of oscillators that the probe has, to be output, wherein the number of oscillators used in the second subset is greater than the number of oscillators used in the first subset,
wherein the number of the oscillators transmitting the ultrasonic waves is the same as the number of oscillators used in the second subset in each of the static image mode and the moving image mode.

9. An ultrasonic diagnostic system, comprising:
an ultrasonic diagnostic apparatus; and
a terminal apparatus, wherein
the ultrasonic diagnostic apparatus includes
a probe configured to transmit ultrasonic waves to a living body and receive ultrasonic waves reflected by the living body; and
a processor configured to:
in a moving image mode, cause ultrasonic image data based on ultrasonic waves received by a first subset of the total number of oscillators that the probe has, to be output, and
in a static image mode, cause ultrasonic image data based on ultrasonic waves received by a second subset of the total number of oscillators that the probe has, to be output, wherein the number of oscillators used in the second subset is greater than the number of oscillators used in the first subset,
wherein the number of the oscillators transmitting the ultrasonic waves is the same as the number of oscillators used in the second subset in each of the static image mode and the moving image mode.

10. An ultrasonic diagnostic apparatus, comprising:
a probe configured to transmit ultrasonic waves to a living body and receive ultrasonic waves reflected by the living body; and
a processor configured to:
in a moving image mode, cause ultrasonic image data based on ultrasonic waves received by a first subset of the total number of oscillators that the probe has to be output, and
in a static image mode, cause ultrasonic image data based on ultrasonic waves received by a second subset of the total number of oscillators that the probe has, to be output, wherein the number of oscillators used in the second subset is greater than the number of oscillators used in the first subset,
wherein the first subset of oscillators is at a center of the second subset of oscillators with respect to a direction in which the second subset of oscillators selected from among the total number of oscillators is arranged, and
the number of the oscillators transmitting the ultrasonic waves is the same as the number of oscillators used in the second subset in each of the static image mode and the moving image mode.

11. An ultrasonic diagnostic apparatus, comprising:
a probe configured to transmit ultrasonic waves to a living body and receive ultrasonic waves reflected by the living body; and
a processor configured to:
in a moving image mode, cause ultrasonic image data based on ultrasonic waves received by a first subset of the total number of oscillators that the probe has to be output, and
in a static image mode, cause ultrasonic image data based on ultrasonic waves received by a second subset of the total number of oscillators that the probe has, to be output, wherein the number of oscillators used in the second subset is greater than the number of oscillators used in the first subset,
wherein the moving image mode denotes a state starting at receiving an instruction to start the probe's scanning of the living body and ending at receiving an instruction to stop the scanning,
the static image mode denotes a state where, after the instruction to stop the scanning is received, the ultrasonic image data based on the ultrasonic waves received by the second subset of oscillators is displayed on a display, and
the number of the oscillators transmitting the ultrasonic waves is the same as the number of oscillators used in the second subset in each of the static image mode and the moving image mode.

* * * * *